United States Patent
Zhao et al.

(10) Patent No.: US 8,394,942 B2
(45) Date of Patent: *Mar. 12, 2013

(54) NUCLEIC ACID ENCODING A SILK PROTEIN AND A METHOD OF PRODUCING A SILK THREAD USING SAME

(75) Inventors: Tianfu Zhao, Kitakatsuragi-gun (JP); Masao Nakagaki, Ueda (JP)

(73) Assignee: Okamoto Corporation, Nara (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/524,120

(22) Filed: Jun. 15, 2012

(65) Prior Publication Data

US 2012/0276590 A1 Nov. 1, 2012

Related U.S. Application Data

(62) Division of application No. 13/226,964, filed on Sep. 7, 2011, now Pat. No. 8,222,479.

(30) Foreign Application Priority Data

Sep. 10, 2010 (JP) .................................. 2010-203558

(51) Int. Cl.
*C12N 15/12* (2006.01)
*C12N 15/85* (2006.01)
*A01K 67/04* (2006.01)
*C12P 21/00* (2006.01)

(52) U.S. Cl. ................... 536/23.5; 435/69.1; 435/320.1; 800/4

(58) Field of Classification Search .................. None
See application file for complete search history.

(56) References Cited

U.S. PATENT DOCUMENTS

| | | | |
|---|---|---|---|
| 5,989,894 | A | 11/1999 | Lewis et al. |
| 5,994,099 | A | 11/1999 | Lewis et al. |
| 6,608,242 | B1 | 8/2003 | Yang |
| 6,872,869 | B2 | 3/2005 | Liu et al. |
| 6,965,060 | B2 | 11/2005 | Yang |
| 7,521,228 | B2 | 4/2009 | Lewis et al. |
| 7,659,112 | B2 | 2/2010 | Hiramatsu et al. |
| 7,723,109 | B2 | 5/2010 | Lewis |
| 7,754,851 | B2 | 7/2010 | Scheibel et al. |
| 7,951,908 | B2 | 5/2011 | Scheibel et al. |

(Continued)

FOREIGN PATENT DOCUMENTS

| CN | 1563085 A | 1/2005 |
|---|---|---|
| EP | 1413585 A2 | 4/2004 |

(Continued)

OTHER PUBLICATIONS

P. Tijssen, "Laboratory Techniques in Biochemistry and Molecular Biology-Hybridization with Nucleic Acid Probes Part I, Chapter 2, "Overview of principles of Hybrization and the Strategy of Nucleic Acid Probe Assay,"", Elsevier, New York, 1993, pp. 19-78.

(Continued)

*Primary Examiner* — Manjunath Rao
*Assistant Examiner* — William W Moore
(74) *Attorney, Agent, or Firm* — Sughrue Mion, PLLC

(57) ABSTRACT

The present invention relates to a recombinant organism having any one of nucleic acids (i) to (iv) introduced therein: (i) a nucleic acid having a base sequence of SEQ ID NO: 1; (ii) a nucleic acid encoding a protein having an amino acid sequence of SEQ ID NO: 2; (iii) a nucleic acid encoding a dragline protein and having a sequence identity of 90% or more with the nucleic acid (i); (iv) a nucleic acid which encodes a dragline protein and hybridizes with a complementary chain of the nucleic acid (i) under stringent conditions.

3 Claims, 4 Drawing Sheets

(A)

(B)

U.S. PATENT DOCUMENTS

| | | |
|---|---|---|
| 2008/0287651 A1 | 11/2008 | Hiramatsu et al. |
| 2009/0205059 A1 | 8/2009 | Brigham |
| 2011/0021757 A1 | 1/2011 | Tamura et al. |

FOREIGN PATENT DOCUMENTS

| | | |
|---|---|---|
| EP | 1712561 A1 | 10/2006 |
| JP | 2002-506642 A | 3/2002 |
| JP | 2004-016144 A | 1/2004 |
| JP | 2005-143428 A | 6/2005 |
| JP | 2005-168460 A | 6/2005 |
| JP | 2007-259775 A | 10/2007 |
| JP | 2008-187947 A | 8/2008 |
| WO | 99/47661 A2 | 9/1999 |
| WO | 02/099082 A2 | 12/2002 |
| WO | 03/020916 A2 | 3/2003 |
| WO | 2005/068495 A1 | 7/2005 |
| WO | 2008/154547 A2 | 12/2008 |

OTHER PUBLICATIONS

Sambrook and Russell, "Molecular Cloning—A Laboratory Manual," vol. 1, Third Edition, 2001. pp. 6.4-6.11.

European Patent Office, European Search Report issued in corresponding EP Application No. 11179742.9, dated Dec. 30, 2011.

Hu et al., "Molecular Mechanisms of Spider Silk," Cell. Mol. Life Sci., 2006, vol. 63, pp. 1986-1998.

Zhao et al., "Novel Molecular and Mechanical Properties of Egg Case Silk from Wasp Spider, *Argiope bruennichi*," Biochemistry, 2006, vol. 45, pp. 3348-3356.

Lawrence et al., "Molecular and Mechanical Properties of Major Ampullate Silk of the Black Widow Spider, *Latrodectus hesperus*," Biomacromolecules, 2004, vol. 5, pp. 689-695.

Fig. 2

Spider Gene Expression Cassette—TTAAAACTCAAAACTTTACTAAATGACGTAAACCGAGCCG (SEQ ID NO: 13)

(A)

(B)

SEQUENCE LISTING

<160> NUMBER OF SEQ ID NOS: 13

<210> SEQ ID NO 1
<211> LENGTH: 2835
<212> TYPE: DNA
<213> ORGANISM: Argiope bruennichi

<400> SEQUENCE: 1

```
ggagcagcca gtgccgctgc agccgctggc ggtcaaggag gacgaggagg atttggcgga      60
ttaggttctc aaggagaagg tggtgccggt caaggaggag caggagccgc agctgctgca     120
gctgcagccg gtgcagatgg cggttttgga ttaggaggct atggtgcggg acgaggttat     180
ggagccggtt taggaggtgc aggtggagct ggagcagcca gtgccgctgc agccgctggc     240
ggtcaaggag gacgaagcgg atttggcgga ttaggttctc aaggagcagg tggtgccggt     300
caaggaggag caggagccgc agctgctgca gctgcagccg gtgcagatgg cggttctgga     360
ttaggaggct atggtgcggg acgaggatat ggagccagtt taggaggtgc agatggagct     420
ggagcagcca gtgccgctgc agccgctggc ggtcaaggag gacgaggagg atttggcgga     480
ttaggttctc aaggagcagg tggtgccggt caaggaggag caggagccgc agctgctgca     540
gctgcagcca gtggagatgg cggttctgga ttaggaggct atggtgcggg acgaggatat     600
ggagccggtt taggaggtgc aggtggagct ggagcagcca gtgccgctgc agccgctggc     660
ggtgaaggag gacgaggcgg atttggcgga ttaggtgctc aaggagcagg tggtgccggt     720
caaggaggat cgttagccgc agctgctgca gctgcagccg gtgcagatgg cggttctgga     780
ttaggaggct atggtgcggg acgaggatat ggagccggtt taggaggtgc agatggagct     840
ggagcagcca gtgccgctgc agccgctggc ggtcaaggag gacgaggagg atttggcaga     900
ttaggttctc aaggagcagg tggtgccggt caaggaggag caggagccgc agctgccgta     960
gctgcagccg gtggagatgg cggttctgga ttaggaggct atggtgcggg acgaggatat    1020
ggagccggtt taggaggtgc aggtggagct ggagcagcca gtgccgctgc agccgctggc    1080
ggtcaaggag gacgaggagg atttggcgga ttaggttctc aaggagcagg tggtgccggt    1140
caaggaggag caggagctgc agctagtgga gatggcggtt ctggattagg aggctatggt    1200
gcgggacgag gatatggagc cggtttagga ggtgcagatg gagctggagc agccagtgcc    1260
gcttcagccg ctggcggtca aggaggacga ggaggatttg gcggattagg ttctcaagga    1320
gcaggtggtg ccggtcaagg aggagcagga gccgcagctg ctgcagctac agccggtgga    1380
gatggcggtt ctggattagg aggctatggt gcgggacgag gttatggagc cggtttagga    1440
```

-continued

```
ggtgcaggtg gagctggagc agccagtgcc gctgcagccg ctggcggtca aggaggacga    1500
ggcggatttg gcggattagg ttctcaagga gcaggtggtg ccggtcaagg aggagcagga    1560
gccgcagctg ctgcagctgc agccggtgga gatggcggtt ctggattagg aggctatggt    1620
gcgggacgag gacatggagt cggtttagga ggtgcaggtg gagctggagc agccagtgcc    1680
gctgcagccg ctggcggtca aggaggacga ggcggatttg gcggattagg ttctcaagga    1740
gcaggtggtg ccggtcaagg aggagcagga gccgcagctg ctgcagctgc agccggtgga    1800
gatggcggtt ctggattagg aggctatggt gcgggacgag gacatggagc cggtttagga    1860
ggtgcaggtg gagctggagc agccagtgcc gctgcagccg ctggcggtca aggaggacga    1920
ggcggatttg gcggattagg ttctcaagga tcaggtggtg ccggtcaagg aggatcggga    1980
gccgcagccg ctgctgctgc agctggtgga gatggcggtt ctggattagg aggctatggg    2040
gcgggacgag gatatggagc tggtttagga ggtgcaggtg gagctggagc agccagtgcc    2100
gctgcagccg ctggcggtca aggaggacga ggcggatttg gcggattagg ttctcaagga    2160
gcaggtggtg ccggtcaagg aggatcagga gccgcagccg ctgctgctgc agctgttgca    2220
gatggcggtt ctggattagg aggctatggt gcgggacgag gatatggagc cggtttagga    2280
ggtgcaggtg gagctggagc tgccagtgcc gctgcagcca ctggcggtca aggaggacga    2340
ggtggatttg gcggattaag ttctcaagga gcaggtggtg ccggtcaagg aggatcggga    2400
gccgcagccg ctgctgctgc agccggtgga gatggcggtt ctggattagg agactatggt    2460
gcgggacgag gatatggagc cggtttagga ggtgcaggtg gagctggagt agccagtgcc    2520
gctgcttccg ctgctgcttc acgcttatca tcacctagtg ctgcttccag agtctcttcc    2580
gctgttacat ctttgatatc aggtggcggc ccaactaatc ctgcagcgtt atctaatact    2640
tttagcaatg ttgtttatca aattagtgta agtagtcccg gtctctctgg ctgtgatgtt    2700
cttatacaag cttactggaa actcgtttcg gctttggtac atattcttgg ttctgctatc    2760
attgggcaag ttaattccag cgctgctgga gaatcagctt cattggttgg acaatccgta    2820
taccaagctt tctct                                                     2835
```

<210> SEQ ID NO 2
<211> LENGTH: 945
<212> TYPE: PRT
<213> ORGANISM: Argiope bruennichi

<400> SEQUENCE: 2

```
Gly Ala Ala Ser Ala Ala Ala Ala Gly Gly Gln Gly Gly Arg Gly
1               5                   10                  15

Gly Phe Gly Gly Leu Gly Ser Gln Gly Glu Gly Gly Ala Gly Gln Gly
            20                  25                  30

Gly Ala Gly Ala Ala Ala Ala Ala Ala Ala Gly Ala Asp Gly Gly
        35                  40                  45

Phe Gly Leu Gly Gly Tyr Gly Ala Arg Gly Tyr Gly Ala Gly Leu
    50                  55                  60

Gly Gly Ala Gly Gly Ala Gly Ala Ala Ser Ala Ala Ala Ala Gly
65                  70                  75                  80

Gly Gln Gly Gly Arg Ser Gly Phe Gly Gly Leu Gly Ser Gln Gly Ala
            85                  90                  95

Gly Gly Ala Gly Gln Gly Gly Ala Gly Ala Ala Ala Ala Ala Ala
        100                 105                 110

Ala Gly Ala Asp Gly Gly Ser Gly Leu Gly Gly Tyr Gly Ala Gly Arg
    115                 120                 125
```

-continued

Gly Tyr Gly Ala Ser Leu Gly Ala Asp Gly Ala Gly Ala Ala Ser
            130                 135                 140
Ala Ala Ala Ala Ala Gly Gly Gln Gly Gly Arg Gly Gly Phe Gly Gly
145                 150                 155                 160
Leu Gly Ser Gln Gly Ala Gly Gly Ala Gly Gln Gly Gly Ala Gly Ala
                165                 170                 175
Ala Ala Ala Ala Ala Ala Ala Ser Gly Asp Gly Gly Ser Gly Leu Gly
            180                 185                 190
Gly Tyr Gly Ala Gly Arg Gly Tyr Gly Ala Gly Leu Gly Gly Ala Gly
            195                 200                 205
Gly Ala Gly Ala Ala Ser Ala Ala Ala Ala Gly Gly Glu Gly Gly
        210                 215                 220
Arg Gly Gly Phe Gly Gly Leu Gly Ala Gln Gly Ala Gly Gly Ala Gly
225                 230                 235                 240
Gln Gly Gly Ser Leu Ala Ala Ala Ala Ala Ala Gly Ala Asp
                245                 250                 255
Gly Gly Ser Gly Leu Gly Gly Tyr Gly Ala Gly Arg Gly Tyr Gly Ala
                260                 265                 270
Gly Leu Gly Gly Ala Asp Gly Ala Gly Ala Ser Ala Ala Ala
            275                 280                 285
Ala Gly Gly Gln Gly Gly Arg Gly Gly Phe Gly Arg Leu Gly Ser Gln
            290                 295                 300
Gly Ala Gly Gly Ala Gly Gln Gly Gly Ala Gly Ala Ala Ala Ala Val
305                 310                 315                 320
Ala Ala Ala Gly Gly Asp Gly Gly Ser Gly Leu Gly Gly Tyr Gly Ala
                325                 330                 335
Gly Arg Gly Tyr Gly Ala Gly Leu Gly Gly Ala Gly Gly Ala Gly Ala
            340                 345                 350
Ala Ser Ala Ala Ala Ala Ala Gly Gly Gln Gly Gly Arg Gly Gly Phe
        355                 360                 365
Gly Gly Leu Gly Ser Gln Gly Ala Gly Gly Ala Gly Gln Gly Gly Ala
        370                 375                 380
Gly Ala Ala Ala Ser Gly Asp Gly Gly Ser Gly Leu Gly Gly Tyr Gly
385                 390                 395                 400
Ala Gly Arg Gly Tyr Gly Ala Gly Leu Gly Gly Ala Asp Gly Ala Gly
                405                 410                 415
Ala Ala Ser Ala Ala Ser Ala Ala Gly Gly Gln Gly Gly Arg Gly Gly
            420                 425                 430
Phe Gly Gly Leu Gly Ser Gln Gly Ala Gly Gly Ala Gly Gln Gly Gly
        435                 440                 445
Ala Gly Ala Ala Ala Ala Ala Thr Ala Gly Gly Asp Gly Gly Ser
        450                 455                 460
Gly Leu Gly Gly Tyr Gly Ala Gly Arg Gly Tyr Gly Ala Gly Leu Gly
465                 470                 475                 480
Gly Ala Gly Gly Ala Gly Ala Ala Ser Ala Ala Ala Ala Gly Gly
                485                 490                 495
Gln Gly Gly Arg Gly Gly Phe Gly Gly Leu Gly Ser Gln Gly Ala Gly
            500                 505                 510
Gly Ala Gly Gln Gly Gly Ala Gly Ala Ala Ala Ala Ala Ala Ala
            515                 520                 525
Gly Gly Asp Gly Gly Ser Gly Leu Gly Gly Tyr Gly Ala Gly Arg Gly
            530                 535                 540
His Gly Val Gly Leu Gly Gly Ala Gly Gly Ala Gly Ala Ala Ser Ala

```
                    545                 550                 555                 560
Ala Ala Ala Ala Gly Gly Gln Gly Gly Arg Gly Gly Phe Gly Gly Leu
                565                 570                 575
Gly Ser Gln Gly Ala Gly Gly Ala Gly Gln Gly Gly Ala Gly Ala Ala
                580                 585                 590
Ala Ala Ala Ala Ala Ala Gly Gly Asp Gly Gly Ser Gly Leu Gly Gly
                595                 600                 605
Tyr Gly Ala Gly Arg Gly His Gly Ala Gly Leu Gly Gly Ala Gly Gly
            610                 615                 620
Ala Gly Ala Ala Ser Ala Ala Ala Ala Gly Gly Gln Gly Gly Arg
625                 630                 635                 640
Gly Gly Phe Gly Gly Leu Gly Ser Gln Gly Ser Gly Gly Ala Gly Gln
                645                 650                 655
Gly Gly Ser Gly Ala Ala Ala Ala Ala Ala Ala Gly Gly Asp Gly
                660                 665                 670
Gly Ser Gly Leu Gly Gly Tyr Gly Ala Gly Arg Gly Tyr Gly Ala Gly
            675                 680                 685
Leu Gly Gly Ala Gly Gly Ala Gly Ala Ala Ser Ala Ala Ala Ala
    690                 695                 700
Gly Gly Gln Gly Gly Arg Gly Gly Phe Gly Gly Leu Gly Ser Gln Gly
705                 710                 715                 720
Ala Gly Gly Ala Gly Gln Gly Gly Ser Gly Ala Ala Ala Ala Ala
                725                 730                 735
Ala Ala Val Ala Asp Gly Gly Ser Gly Leu Gly Gly Tyr Gly Ala Gly
                740                 745                 750
Arg Gly Tyr Gly Ala Gly Leu Gly Gly Ala Gly Gly Ala Gly Ala Ala
            755                 760                 765
Ser Ala Ala Ala Ala Thr Gly Gly Gln Gly Gly Arg Gly Gly Phe Gly
    770                 775                 780
Gly Leu Ser Ser Gln Gly Ala Gly Gly Ala Gly Gln Gly Gly Ser Gly
785                 790                 795                 800
Ala Ala Ala Ala Ala Ala Ala Gly Gly Asp Gly Gly Ser Gly Leu
                805                 810                 815
Gly Asp Tyr Gly Ala Gly Arg Gly Tyr Gly Ala Gly Leu Gly Gly Ala
            820                 825                 830
Gly Gly Ala Gly Val Ala Ser Ala Ala Ala Ser Ala Ala Ser Arg
    835                 840                 845
Leu Ser Ser Pro Ser Ala Ala Ser Arg Val Ser Ser Ala Val Thr Ser
850                 855                 860
Leu Ile Ser Gly Gly Gly Pro Thr Asn Pro Ala Ala Leu Ser Asn Thr
865                 870                 875                 880
Phe Ser Asn Val Val Tyr Gln Ile Ser Val Ser Ser Pro Gly Leu Ser
                885                 890                 895
Gly Cys Asp Val Leu Ile Gln Ala Leu Leu Glu Leu Val Ser Ala Leu
            900                 905                 910
Val His Ile Leu Gly Ser Ala Ile Ile Gly Gln Val Asn Ser Ser Ala
    915                 920                 925
Ala Gly Glu Ser Ala Ser Leu Val Gly Gln Ser Val Tyr Gln Ala Phe
    930                 935                 940
Ser
945

<210> SEQ ID NO 3
<211> LENGTH: 39
```

```
<212> TYPE: DNA
<213> ORGANISM: Artificial
<220> FEATURE:
<223> OTHER INFORMATION: inner primer

<400> SEQUENCE: 3
cgactcacta tagggaattc cttaactagt ggagcagcc                              39

<210> SEQ ID NO 4
<211> LENGTH: 35
<212> TYPE: DNA
<213> ORGANISM: Artificial
<220> FEATURE:
<223> OTHER INFORMATION: inner primer

<400> SEQUENCE: 4
gacaatccgt ataccaagct ttctctgcta gctag                                  35

<210> SEQ ID NO 5
<211> LENGTH: 22
<212> TYPE: DNA
<213> ORGANISM: Artificial
<220> FEATURE:
<223> OTHER INFORMATION: inner primer

<400> SEQUENCE: 5
aagcttgttg tacaaaactg cc                                                22

<210> SEQ ID NO 6
<211> LENGTH: 24
<212> TYPE: DNA
<213> ORGANISM: Artificial
<220> FEATURE:
<223> OTHER INFORMATION: inner primer

<400> SEQUENCE: 6
tgcagcacta gtgctgaaat cgct                                              24

<210> SEQ ID NO 7
<211> LENGTH: 28
<212> TYPE: DNA
<213> ORGANISM: Artificial
<220> FEATURE:
<223> OTHER INFORMATION: inner primer

<400> SEQUENCE: 7
ctagctagca gttacggagc tggcaggg                                          28

<210> SEQ ID NO 8
<211> LENGTH: 33
<212> TYPE: DNA
<213> ORGANISM: Artificial
<220> FEATURE:
<223> OTHER INFORMATION: inner primer

<400> SEQUENCE: 8
cgggatccta gtacattcaa ataaaatgca tac                                    33

<210> SEQ ID NO 9
<211> LENGTH: 30
<212> TYPE: DNA
<213> ORGANISM: Artificial
<220> FEATURE:
<223> OTHER INFORMATION: inner primer

<400> SEQUENCE: 9
cttgaccttg ccacagagga ctattagagg                                        30
```

```
<210> SEQ ID NO 10
<211> LENGTH: 30
<212> TYPE: DNA
<213> ORGANISM: Artificial
<220> FEATURE:
<223> OTHER INFORMATION: inner primer

<400> SEQUENCE: 10
cagtgacact taccgcattg acaagcacgc                                        30

<210> SEQ ID NO 11
<211> LENGTH: 29
<212> TYPE: DNA
<213> ORGANISM: Artificial
<220> FEATURE:
<223> OTHER INFORMATION: inner primer

<400> SEQUENCE: 11
cctcgatata cagaccgata aaacacatg                                         29

<210> SEQ ID NO 12
<211> LENGTH: 29
<212> TYPE: DNA
<213> ORGANISM: Artificial
<220> FEATURE:
<223> OTHER INFORMATION: inner primer

<400> SEQUENCE: 12
gtcagtcaga acaactttg gcacatatc                                          29

<210> SEQ ID NO 13
<211> LENGTH: 40
<212> TYPE: DNA
<213> ORGANISM: Bombyx mori

<400> SEQUENCE: 13
ttaaaactca aactttact aaatgacgta aaccgagccg                              40
```

US 8,394,942 B2

NUCLEIC ACID ENCODING A SILK PROTEIN AND A METHOD OF PRODUCING A SILK THREAD USING SAME

This application is a divisional of U.S. patent application Ser. No. 13/226,964 filed Sep. 7, 2011 (now U.S. Pat. No. 8,222,479) which claims the benefit of Japanese Patent Application No. 2010-203558, filed on Sep. 10, 2010, in the Japanese Patent Office, the disclosures of which are incorporated herein in their entireties by reference.

BACKGROUND OF THE INVENTION

1. Field of the Invention

The present invention relates to a recombinant organism and a protein produced by the recombinant organism.

2. Related Background Art

As a natural fiber with an excellent strength, spider silk has drawn an attention. However, spiders eat each other and thus are not suitable for farming in a same place, and the amount of spider silk obtained from a single spider is low. In addition, a spider uses different types of silk threads according to its needs. Therefore, a mass production of spider silk is difficult.

Then, an attempt has been made to introduce a gene encoding a spider silk protein into an organism excluding a spider by use of a gene recombinant technique to produce spider silk. For example, a method of producing a spider silk protein in a genetically modified goat and obtaining the spider silk protein from milk of the goat is disclosed (Patent Literature 1: Japanese Unexamined Patent Application Publication No. 2002-506642). However, according to the method, the spider silk protein needs to be extracted, purified and artificially spun, being problematic in the points of labor, cost and environmental load due to a solvent.

To solve the aforementioned problems, an attempt has been made to introduce a gene encoding a spider silk protein into a silkworm to produce the spider silk protein (Patent Literature 2: WO2005/068495). By a recombinant silkworm, the spider silk protein is ejected as a silk thread, and therefore the aforementioned treatments such as extraction, purification and spinning are unnecessary.

SUMMARY OF THE INVENTION

However, physical properties of silk threads produced by conventional recombinant silkworms have been far inferior to those of native spider silks, and the silk threads have been unsatisfactory in their strength.

Then, the present invention aims to provide a recombinant organism producing a protein with excellent physical properties and a protein with excellent physical properties produced by the recombinant organism. Furthermore, the present invention aims to provide a recombinant silkworm producing a silk thread with a sufficiently excellent strength and a silk thread with sufficiently excellent strength produced by the recombinant silkworm.

The present inventors intensively studied with a view to achieving the aforementioned aims, and, as a result, found that when a gene of *Argiope bruennichi* is introduced into an organism to be genetically modified, the resultant protein has excellent physical properties, and thereby completed the present invention.

More specifically, the present invention relates to a recombinant organism having any one of the following nucleic acids (i) to (iv) introduced therein and a protein produced by the recombinant organism:

(i) a nucleic acid having a base sequence of SEQ ID NO: 1;
(ii) a nucleic acid encoding a protein having an amino acid sequence of SEQ ID NO: 2;
(iii) a nucleic acid encoding a dragline protein and having a sequence identity of 90% or more with the nucleic acid (i);
(iv) a nucleic acid which encodes a dragline protein and hybridizes with a complementary chain of the nucleic acid (i) under stringent conditions.

By introducing the aforementioned specific nucleic acid, a protein produced by the recombinant organism becomes rich in the spider protein and, as a result, becomes excellent in physical properties such as strength.

Particularly, the present invention relates to a recombinant silkworm having any one of the aforementioned nucleic acids (i) to (iv) introduced therein, a protein produced by the recombinant silkworm and a silk thread produced by the recombinant silkworm. By introducing the aforementioned specific nucleic acid into a silkworm, a silk thread produced by the recombinant silkworm is rich in spider protein and, as a result, has a sufficient strength.

According to the present invention, it is possible to provide a recombinant organism which produces a protein with excellent physical properties, and a protein with excellent physical properties produced by the recombinant organism. Furthermore, according to in an embodiment, it is possible to provide a recombinant silkworm which produces a silk thread with a sufficiently excellent strength and a silk thread with a sufficiently excellent strength produced by the recombinant silkworm.

BRIEF DESCRIPTION OF THE DRAWINGS

In FIG. 1, legends have the following meanings: FP: Silkworm fibroin H-chain gene promoter; MASP: Spider gene; FC: C-terminal partial sequence of the silkworm fibroin H-chain gene; MK: Marker gene; L: PiggyBac transposon L-hand; and R: PiggyBac transposon R-hand.

FIG. 2 is a view showing a genome sequence of a silkworm downstream of the site at which a spider gene expression cassette is inserted.

DESCRIPTION OF THE PREFERRED EMBODIMENTS

Figure 1:
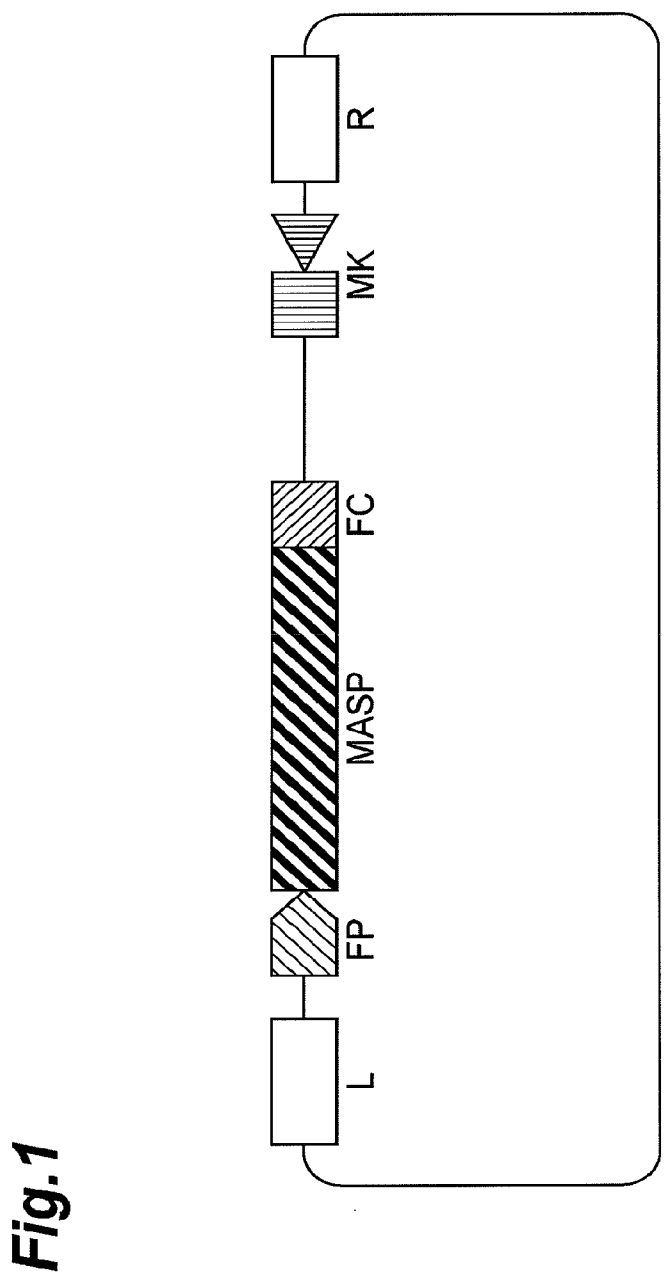
FIG. 1 is a schematic view showing the structure of a vector plasmid for genetic recombination.

An embodiment for performing the invention will be described below, if necessary, referring to the accompanying drawings. However, the present invention is not limited to the following embodiment.

The present invention relates to a recombinant organism having any one of the following nucleic acids (i) to (iv) introduced therein and a protein produced by the recombinant organism:

(i) a nucleic acid having a base sequence of SEQ ID NO: 1;
(ii) a nucleic acid encoding a protein having an amino acid sequence of SEQ ID NO: 2;
(iii) a nucleic acid encoding a dragline protein and having a sequence identity of 90% or more with the nucleic acid (i);

(iv) a nucleic acid which encodes a dragline protein and hybridizes with a complementary chain of the nucleic acid (i) under stringent conditions.

Particularly, the present invention relates to a recombinant silkworm having any one of the aforementioned nucleic acids (i) to (iv) introduced therein, a protein produced by the recombinant silkworm and a silk thread produced by the recombinant silkworm.

A nucleic acid having the base sequence of SEQ ID NO: 1 is a nucleic acid encoding MaSp1 (major ampullate spidroin 1) protein, which is a main component of a dragline (or warp) protein of *Argiope bruennichi*, and may be artificially synthesized or obtained from a genomic library or a cDNA library, or may be obtained by amplifying each of these nucleic acids by PCR and obtained by digestion with a restriction enzyme(s), as long as a nucleic acid has the base sequence of SEQ ID NO: 1.

The amino acid sequence of SEQ ID NO: 2 is the amino acid sequence of the MaSp1 protein of *Argiope bruennichi*.

As the nucleic acid to be introduced into a silkworm, a nucleic acid (iii) having a sequence identity of 90% or more with the nucleic acid having a base sequence of SEQ ID NO: 1 may be used as long as it encodes a dragline protein. The sequence identity may be 90% or more, but is preferably 95% or more and more preferably 98% or more.

Furthermore, the nucleic acid to be introduced into a silkworm may be a nucleic acid (iv) which hybridizes with a complementary chain of a nucleic acid having the base sequence of SEQ ID NO: 1 under stringent conditions as long as the nucleic acid encodes a dragline protein. Herein, "complementary chain" of a nucleic acid refers to a nucleotide sequence which pairs through hydrogen bonding between nucleic acid bases (for example, T to A, C to G). Furthermore, "hybridize" means to form a complementary bonding between complementary chains or form interaction between bases of single-strand nucleic acid molecules.

"Stringent conditions" mentioned above refers to conditions under which a complementary chain of a nucleotide chain having a homology with a target sequence preferentially hybridizes with the target sequence and a complementary chain of a nucleotide chain having no homology does not substantially hybridize. The stringent conditions are dependent upon the sequence and vary depending upon various situations. As a sequence becomes longer, specific hybridization thereof occurs at a further higher temperature. Generally, for stringent conditions, a temperature is selected so that it is about 5° C. lower than the thermal melting temperature ($T_m$) of a specific sequence at a predetermined ion strength and pH. $T_m$ is the temperature at which 50% of complementary nucleotides to a target sequence hybridize with the target sequence in an equilibrium state at a predetermined ion strength, pH and nucleic acid concentration. "Stringent conditions" are dependent upon the sequence and vary depending upon various environmental parameters. A general principle of nucleic acid hybridization can be found in Tijssen (Tijssen (1993), Laboratory Techniques In Biochemistry And Molecular Biology-Hybridization With Nucleic Acid Probes Part I, Chapter 2 "Overview of principles of hybridization and the strategy of nucleic acid probe assay", Elsevier, N.Y.).

Typically, the stringent conditions are those in which the salt concentration is less than about 1.0 M $Na^+$, typically about 0.01 to 1.0 M of $Na^+$ concentration (or another salt) at pH 7.0 to 8.3; and the temperature is at least about 30° C. for a short nucleotide (for example, 10 to 50 nucleotides) and at least about 60° C. for a long nucleotide (for example, longer than 50 nucleotides). The stringent conditions can be also achieved by addition of a destabilizing agent such as formamide. The stringent conditions referred in this specification include hybridization in a buffer solution of 50% formamide, 1M NaCl, 1% SDS (37° C.) and washing with 0.1×SSC at 60° C.

In this specification, the term "recombinant organism" refers to an organism transformed by introducing a foreign gene into the chromosome by means of genetic recombination. The organism to be transformed is not particularly limited and, for example, an insect, an animal, a plant or a microorganism may be used; however, an insect is preferred. Examples of the preferable insect include *Bombyx mori, Bombyx mandarina, Antheraea yamamai* and *Antheraea pernyi*. Among them, *Bombyx mori* and *Bombyx mandarina* belonging to *Bombycidae* are preferably used, and *Bombyx mori* is particularly preferably used.

In this specification, the word "silkworm" refers to *Bombyx mori*. A silkworm may be either a breed for experimentation or a commercial breed commercialized for practical use. Furthermore, the word "recombinant silkworm" refers to a silkworm transformed by introducing a foreign gene into the silkworm chromosome by means of genetic recombination. In an embodiment, genetic recombination is performed by a method using a transposon; however, the method is not limited and any method is used as long as it can introduce a foreign gene into a silkworm and recombination of a gene can be performed by other methods including electroporation.

In this specification, the word "silk thread" is a fiber, which is ejected by *Bombyx mori, Bombyx mandarina, Antheraea yamamai, Antheraea pernyi*, etc., constituting a cocoon and containing a fibroin protein as a main component. The fibroin protein is composed of two large and small subunits (H-chain and L chain).

EXAMPLES

The present invention will be more specifically described by way of Examples. However, the present invention is not limited to the following Examples.

(Spider Gene)
A spider gene was obtained in accordance with a PCR method by using a vector containing a nucleic acid having the base sequence of SEQ ID NO: 1 and primers designed so as to match respectively with two ends of the nucleic acid. To the primers, appropriate restriction enzyme sites are previously provided for the following gene manipulation. More specifically, as a forward primer, MaSp1FW (5'-CGACTCACTAT-AGGGAATTCCTTAACTAGTGGAGCAGCC-3') (SEQ ID NO: 3) was used and as a reverse primer, MaSp1RV (5'-GACAATCCGTATACCAAGCTTTCTCTGCTAGCTAG-3') (SEQ ID NO: 4) was used.

(Silkworm Fibroin H-chain Gene Promoter Sequence)
A silkworm fibroin H-chain gene promoter sequence was obtained in accordance with a PCR method by using primers designed based on the sequence of the silkworm fibroin H-chain gene (GeneBank Registration No. AF226688) and normal silkworm genomic DNA as a template. More specifically, as a forward primer, PfibH5' (5'-AAGCTTGTTGTA-CAAAACTGCC-3') (SEQ ID NO: 5) containing a HindIII restriction enzyme site was used and as a reverse primer, PfibH3' (5'-TGCAGCACTAGTGCTGAAATCGCT-3') (SEQ ID NO: 6) containing a SpeI site was used.

(C-terminal Partial Sequence of Silkworm Fibroin H-chain Gene)
A C-terminal partial sequence of the silkworm fibroin H-chain gene was obtained in accordance with a PCR method by using primers designed based on the sequence of the silkworm fibroin H-chain gene (GeneBank Registration No.

AF226688) and normal silkworm genomic DNA as a template. More specifically, as a forward primer, LBS-FW (5'-CTAGCTAGCAGTTACGGAGCTGGCAGGG-3') (SEQ ID NO: 7) containing a NheI site was used and as a reverse primer, LBS-RV (5'-CGGGATCCTAGTACAT-TCAAATAAAATGCATAC-3') (SEQ ID NO: 8) containing a BamHI site was used.

(Preparation of Vector Plasmid for Genetic Recombination)

The silkworm fibroin H-chain promoter sequence (FP), a spider gene sequence (MASP) and the C-terminal partial sequence of the silkworm fibroin H-chain gene (FC) were sequentially ligated to form a spider gene expression cassette. The spider gene expression cassette was introduced into a vector plasmid containing piggyBac transposon to prepare a vector plasmid for genetic recombination. FIG. 1 is a schematic view showing the structure of the vector plasmid for genetic recombination. The reference symbols of FIG. 1 stand for the followings.

FP: Silkworm fibroin H-chain gene promoter sequence
MASP: Spider gene sequence
FC: C-terminal partial sequence of the silkworm fibroin H-chain gene
MK: Marker gene sequence
L: PiggyBac transposon L-hand
R: PiggyBac transposon R-hand (Preparation of Recombinant Silkworm)

The vector plasmid for genetic recombination was amplified in *Escherichia coli*, and purified by "QIAGEN plasmid Midi Kit" (manufactured by QIAGEN) in accordance with the manual attached the kit. A helper plasmid containing a transposase protein gene was also purified by the above method. DNA of the plasmids purified above were dissolved in TE buffer such that the DNA of the vector plasmid for genetic recombination and the DNA of the helper plasmid were mixed in a ratio of 1:1 and precipitated with ethanol. Finally, the concentration of the DNA mixture was adjusted with a phosphate buffer (pH 7) containing 5 mM KCl to be 400 ng/ul. This was injected to a silkworm egg of 3-6 hour old after egg-laying under microscopic observation.

The egg to which the sample was injected is designated as G0 generation; the G0 generation grew and changed to a moth, which is designated as G0 moth; eggs laid by G0 moth as a parent are designated as G1 eggs. G0 moth was mated with a moth having no injection and G1 eggs were collected; and G1 eggs in the incubation state were observed under a fluorescent microscope and screened for fluorescence-emitting eggs (positive egg). A population of eggs laid by a single parent moth (G0 moth) was treated as a group and the number of groups in which one or more positive eggs were detected was counted and recorded as the "positive G1 number". The results are shown in Table 1.

TABLE 1

| Number of injection eggs | Number of hatched eggs | Hatching rate | Number of Positive G1 (moth) |
|---|---|---|---|
| 6426 | 1200 | 18.7 | 12 |

(Insertion of Spider Gene by Inverse PCR and Confirmation of Insertion Site)

Silkworm genomic DNA was extracted by a known method (see Sambrook and Maniatis, Molecular Cloning-A Laboratory Manual). The genomic DNA was cleaved with restriction enzyme HaeIII and thereafter self-ligated. Using this as a template and two pairs of primers respectively matching with left and right hands of piggyBac, and a fragment containing a silkworm genome sequence of an insertion site was amplified to identify the sequence. More specifically, as a left hand forward primer, BacLF (5'-CTTGACCTTGCCACAGAG-GACTATTAGAGG-3') (SEQ ID NO: 9) was used, as a left hand reverse primer, BacLR (5'-CAGTGACACTTACCG-CATTGACAAGCACGC-3') (SEQ ID NO: 10) was used, as a right hand forward primer, (5'-CCTCGATATACAGAC-CGATAAAACACATG-3') (SEQ ID NO: 11) was used, and a right hand reverse primer, (5'-GTCAGTCAGAAA-CAACTTTGGCACATATC-3') (SEQ ID NO: 12) was used. FIG. 2 shows a silkworm genome sequence (SEQ ID NO: 13) downstream of a site at which a spider gene expression cassette is inserted.

(Protein Analysis of Silk Thread)

Figure 3:
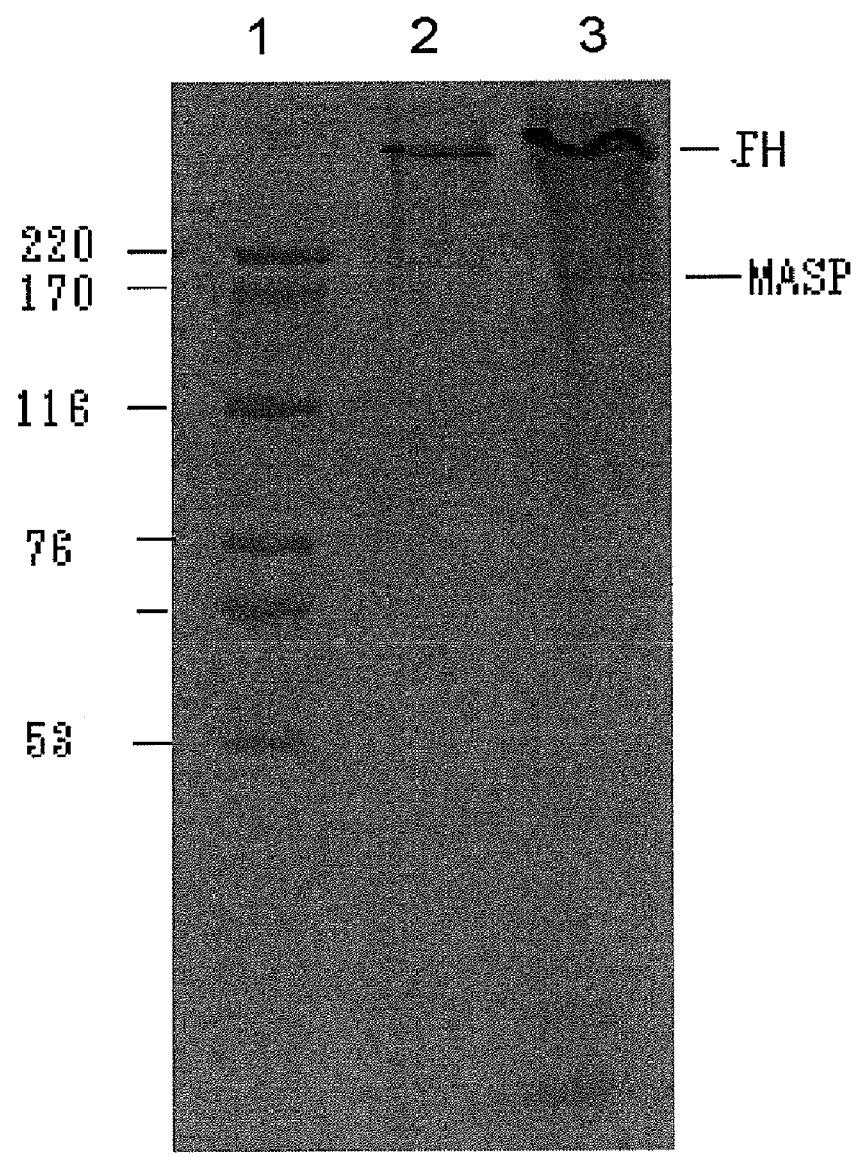
FIG. 3 is a view showing the result of the SDS-PAGE separation of silk thread proteins produced by a recombinant silkworm.

A cocoon produced by a recombinant silkworm was excised, and to 1 mg of cocoon pieces, 50 µl of a 60% LiSCN was added, which was shaken, allowed to stand still at room temperature for 2 hours to solubilize a protein, thereafter, centrifuged at 15000 rpm to remove an unsolved substances, and the supernatant was subjected to SDS-PAGE to separate a spider silk protein and fibroin of a silk worm. FIG. 3 shows the SDS-PAGE separation results of the silk thread protein produced by a recombinant silkworm. In FIG. 3, FH stands for a silkworm fibroin H-chain and MASP stands for a spider silk protein. Furthermore, in FIG. 3, in lane 1, an HMW molecular weight marker was run; in lane 2, the supernatant containing a silk thread protein produced by a recombinant silkworm was run; in lane 3, a solution containing 5 times more protein than that in lane 2 was run. From the separation results, the content of the spider silk protein in the silk thread protein was calculated to be 22.5%, which is a numerical value significantly higher than the content of a conventional recombinant silkworm.

(Determination of Fineness of Silk Thread under Scanning Electron Microscope Observation)

Figure 4:
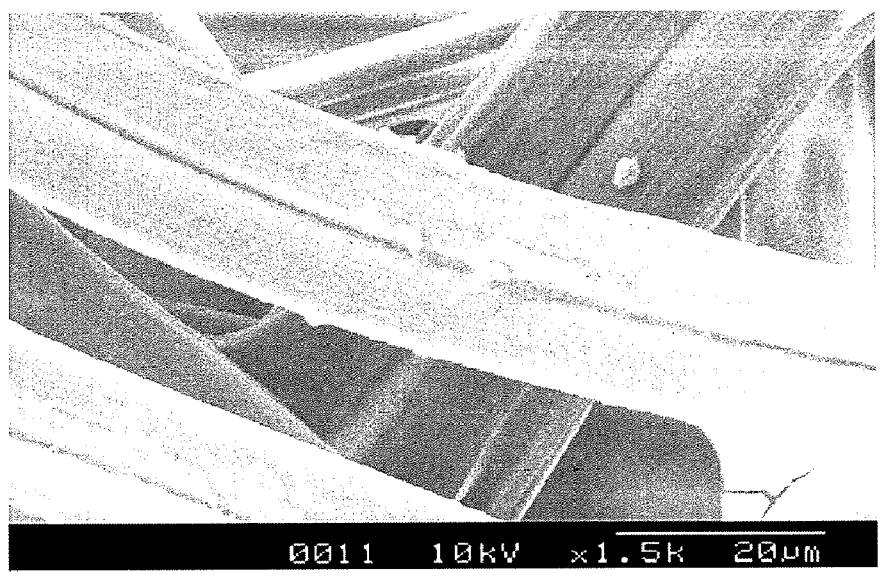
FIG. 4 shows scanning electron micrographs of silk threads of a recombinant silkworm (A) and a non-recombinant silkworm (B).
Figure 4:
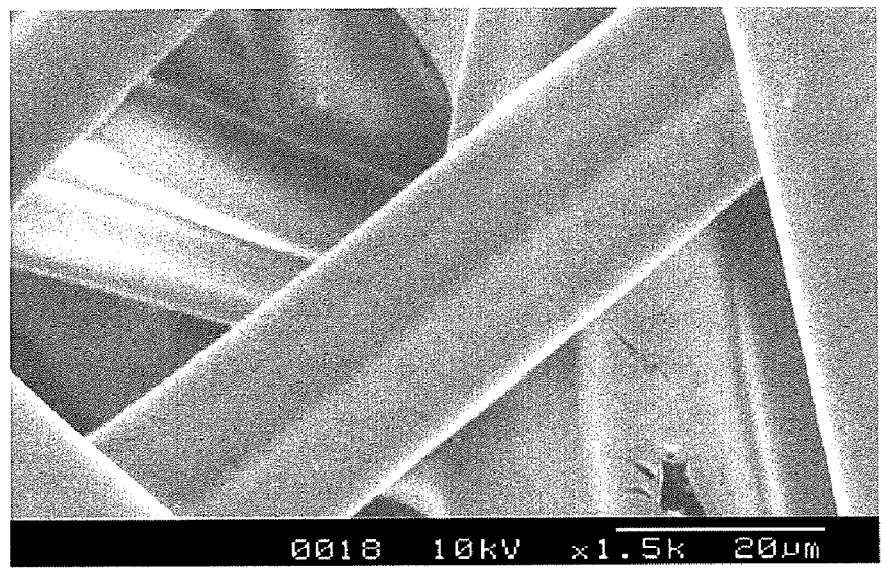

A cocoon produced by a recombinant silkworm was soaked in warm water of 40° C. for one minute, fluff was removed, and thread was carefully collected and acclimated at conditions: 20° C., 65% RH, a day and night to prepare a sample. The obtained sample was observed by SEM (scanning electron microscope) S-2380N (manufactured by Hitachi, Ltd.) at a voltage of 10 kV and photographed. Based on the photograph, the diameter and sectional area of a thread were estimated, and based on the sectional area, the strength of the thread was calculated. As a control, a cocoon of a silkworm (non-recombinant silkworm) not genetically modified was treated in the same manner. FIG. 4 shows scanning electron micrographs of silk threads of a recombinant silkworm (A) and a non-recombinant silkworm (B).

(Analysis of Physical Property of Silk Thread)

The cocoon produced by a recombinant silkworm was soaked in warm water of 40° C. for one minute, fluff was removed, and thread was carefully collected and acclimated at conditions: 20° C., 65% RH, a day and night to prepare a sample. The obtained sample was tested for tensile strength by use of "AUTOGRAPH AGS-J" (manufactured by Shimadzu Corporation) under standard conditions: 20° C., 65% RH. As a control, the silk thread produced by a silkworm (non-recombinant silkworm) not genetically modified was tested for tensile strength in the same manner. As a result, the strength of the silk thread of a control (non-recombinant silkworm) was 397.0 MPa (3.49 g/d), whereas the strength of the silk thread produced by the recombinant silkworm was 489.2 MPa (4.27 g/d), which was increased by 22.35%.

On the other hand, in a conventional recombinant silkworm employing a gene of e.g., *Araneus ventricosus* described in Patent Literature 2, the strength of a control silk thread was 3.78 g/d, whereas the strength of the silk thread of a recombinant silkworm was 3.93 g/d, which was increased only by 3.96% (see Patent Literature 2, page 29, Table 3).

From the foregoing, in the case of using a specific nucleic acid of the present invention, compared to a conventional case of using a gene of e.g. *Araneus ventricosus*, the strength of silk threads produced by the recombinant silkworms was found to clearly increase. Table 2 shows physical properties of the silk thread of the present invention compared to those of the silk thread of Patent Literature 2.

TABLE 2

| | Non-recombinant silkworm thread (g/d) | Recombinant silkworm thread (g/d) | Increased rate of strength (%) | Content of spider-thread protein (%) |
|---|---|---|---|---|
| Patent Literature 2 | 3.78 | 3.93 | 3.96 | 5 |
| Present Invention | 3.49 | 4.27 | 22.35 | 22.5 |

A protein produced by the recombinant organism of the present invention is useful as a naturally occurring material with excellent physical properties. Particularly, the silk thread produced by the recombinant silkworm of the present invention is a naturally occurring material with a sufficiently excellent strength, and thus, the silk thread is preferably used not only in medical supplies such as surgical suture but also various uses such as flight equipment, clothing and cosmetics.

What is claimed is:

1. An isolated nucleic acid selected from the group consisting of
   (i) a nucleic acid having the base sequence of SEQ ID NO:1;
   (ii) a nucleic acid encoding a protein having the amino acid sequence of SEQ ID NO:2;
   (iii) a nucleic acid with a base sequence identity of 90% or more to the nucleic acid sequence of clause (i); and
   (iv) a nucleic acid which encodes a dragline protein and hybridizes with the complementary chain of the nucleic acid of clause (i) under stringent conditions comprising hybridization in a buffer solution of 50% formamide, 1M NaCl, 1% SDS at 37° C. and washing with 0.1×SSC at 60° C.

2. A vector comprising the nucleic acid according to claim 1.

3. A method of producing a silk thread that comprises the dragline protein encoded by the nucleic acid of claim 1 comprising the steps of:
   (i) culturing a recombinant silkworm transformed with the nucleic acid according to claim 1 and
   (ii) collecting the silk thread produced by said recombinant silkworm.

* * * * *